United States Patent [19]

Prisbylla

[11] Patent Number: 4,911,748
[45] Date of Patent: Mar. 27, 1990

[54] HERBICIDAL 5-SUBSTITUTED-3-PHENYL-IMIDAZOLIDINE-2,4-DIONES

[75] Inventor: Michael P. Prisbylla, Richmond, Calif.

[73] Assignee: ICI Americas Inc., Wilmington, Del.

[21] Appl. No.: 289,997

[22] Filed: Dec. 22, 1988

[51] Int. Cl.$^4$ ............................................. A01N 43/50
[52] U.S. Cl. ............................................. 71/92; 71/90; 548/313; 548/314
[58] Field of Search ...................... 71/92, 90; 548/314, 548/313

[56] References Cited

U.S. PATENT DOCUMENTS

| 3,846,441 | 11/1974 | Mine et al. ........................... 71/92 X |
| 4,582,903 | 4/1986 | Mirviss ................................. 544/139 |
| 4,613,691 | 9/1986 | Mirviss et al. ....................... 562/443 |

OTHER PUBLICATIONS

Kirk Othmer, *Encyclopedia of Chemical Technoloogy*, vol. 12, pp. 694–698.

*Primary Examiner*—Richard A. Schwartz
*Attorney, Agent, or Firm*—Denis A. Polyn

[57] ABSTRACT

This invention relates to 5-substituted-3-phenyl-imidazolidine-2,4-diones, to a process for their preparation and to their use in herbicidal formulations.

12 Claims, No Drawings

HERBICIDAL 5-SUBSTITUTED-3-PHENYL-IMIDAZOLIDINE-2,4-DIONES

BACKGROUND AND SUMMARY OF THE INVENTION

This invention relates to 5-substituted-3-phenylimidazolidine-2,4-diones, to a process for their preparation and to their use in herbicidal formulations. In particular, this invention relates to 5-substituted-3-phenylimidazolidine-2,4-diones of the formula I

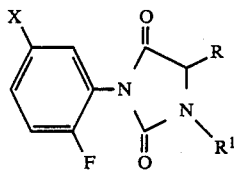

in which:
X is hydrogen or halogen;
R is selected from the group —$R^2$ or =CH—$R^3$;
$R^1$ is methyl or ethyl;
$R^2$ is $C_{1-8}$alkyl, $C_{1-8}$haloalkyl, $C_{3-8}$cycloalkyl, $C_{4-10}$cycloalkylalkyl, phenyl, benzyl or substituted benzyl; and
$R^3$ is $C_{1-8}$alkyl, $C_{3-8}$cycloalkyl, phenyl, substituted phenyl, benzyl, substituted benzyl, styryl, or a heterocyclic group of 3 to 10 ring atoms.

The compounds of the present invention, as will be seen from the description and test data which follow, have utility as both pre-emergence and post-emergence herbicides against a wide range of grassy and broadleaf plant species. The compounds are of particular interest when used against broadleaf plants.

DETAILED DESCRIPTION OF THE INVENTION AND PREFERRED EMBODIMENTS

When used in this specification and in the appended claims, these terms have the following meaning.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn, and dwarfing.

The term "herbicidally effective amount" is used to denote any amount which achieves such inhibitive control or modification when applied to the undesired plants themselves or to the area, or "locus", in which these plants are growing.

The term "plants" is intended to include germinant seeds, emerging seedlings and established vegetation, including both roots and above-ground portions.

Whenever X, $R^2$, or $R^3$ is or comprises halogen, such halogen is conveniently selected from bromo, chloro and fluoro.

The term "alkyl" and all groups containing alkyl portions are intended to include both straight-chain, branched-chain and cyclic groups. Examples are methyl, ethyl, n-propyl, isopropyl, cyclopropyl, n-butyl, isobutyl, sec-butyl, t-butyl, 2-methyl-n-butyl, n-hexyl, cyclohexyl, and cyclopropylmethyl.

The terms "substituted phenyl" and substituted benzyl" refer to a phenyl group or a benzyl group, respectively, substituted at one to three of the ring carbon atoms by, for example, $C_{1-6}$alkyl, $C_{1-6}$haloalkyl, $C_{1-6}$alkoxy, $C_{1-6}$haloalkoxy, halogen, or a methylenedioxy group.

The term "heterocyclic group" refers to a cycloalkyl, a cycloalkenyl or an aryl group of 3 to 10 ring carbon atoms where one to three of the ring carbons is replaced by oxygen, sulfur or nitrogen. Examples of heterocyclic groups include furyl, pyrrolyl, thienyl, and pyridyl.

Within the scope of the above formula, certain embodiments are preferred, as follows.

X is preferably fluoro.

$R^2$ is preferably benzyl or $C_{1-4}$alkyl, either straight or branched.

$R^3$ is preferably $C_{3-6}$cycloalkyl, phenyl, substituted phenyl or a heterocyclic group. It is more preferably cyclohexyl, pyridyl, or phenyl unsubstituted or substituted with methyl, methoxy, trifluoromethyl, chloro, or fluoro.

It will be noted that the generic formula representing the substituted 3-phenyl-imidazolidine-2,4-diones of the present invention indicates two chiral centers. The specific compounds disclosed herein each represent a mixture of enantiomers at both chiral centers, unless otherwise indicated. Herbicidal activity for the mixture is an indication of herbicidal activity for each individual enantiomer. In certain cases, however, one enantiomer will have a greater herbicidal activity than the other enantiomer for a given chiral center.

The compounds of this invention where R is —$R^2$ may be prepared by the process A of reacting together a phenylisocyanate of formula II with an amino acid of formula III in an organic solvent and in the presence of a base such as triethylamine. The resulting imidazolidinedione, unsubstituted at the N-1 position, is then reacted with a halide $R^1$—Q, where Q is a halogen.

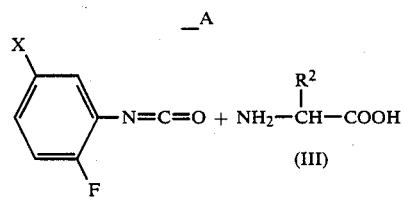

The compounds of this invention where R is =CH—$R^3$ may be prepared by the condensation of a hydantoin, unsubstituted at the N-1 position, with an aldehyde. See, Kirk Othmer, *Encyclopedia of Chemical Technology*, Volume 12, pages 694 and 698. A number of improvements on this method have been reported (see, U.S. Pat. No. 4,582,903 for a discussion). However, this method gives only partial success, particularly when the reaction is with aliphatic aldehydes. Also, difficulty is often encountered when it is attempted to condense N-1 substituted hydantoins with either aromatic or aliphatic aldehydes. See, Kirk Othmer, supra, page 698.

It has now been found that the compounds of formula I where R is =CH—$R^3$ may be prepared by reacting together an aldehyde and a hydantoin substituted with an acetyl group at the N-1 position. Thus, the compounds of formula I where R is =CH—$R^3$ may be prepared by the process B comprising (a) reacting a compound having the formula

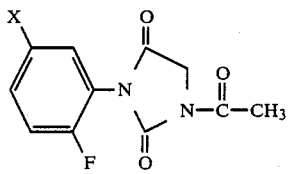

where X is as defined above, with an aldehyde of the formula R³—CHO (V), where R³ is as defined above, to give a compound of the formula

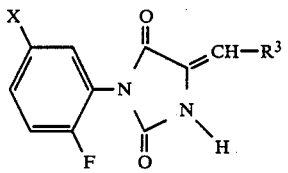

and, (b) reacting the compound of formula VI with a halide R¹—Q, where Q is a halogen.

This process allows the preparation of the compounds of formula I under mild conditions and in good yields.

In the above synthesis, when compound V is an aromatic aldehyde, the N-acetylhydantoin and the aldehyde are reacted together in an organic solvent, in the presence of a base such as triethylamine, at a temperature from ambient temperature to the reflux temperature of the solvent.

In the above synthesis, when compound V is an aliphatic aldehyde, the N-acetylhydantoin and the aldehyde are reacted together in an organic solvent, in the presence of an alkoxide or the salt of an alkoxide such as potassium tert-butoxide, at a temperature from −10° C. to ambient temperature.

Any alkoxide or the salt thereof, such as the sodium or potassium salt, may be used in the above process B of the present invention. Tert-butoxide and the salts thereof are preferred.

Any inert organic solvent can be used in the above two processes A and B, including, but not limited to the following: aliphatic compounds, for example heptane or octane; aromatic compounds, for example benzene, toluene, xylene or mesitylene; chlorinated aliphatic or aromatic compounds, for example methylene chloride, 1,2-dichloroethane or chlorobenzene; ethers, for example 1,2-dimethoxyethane, diethyl ether, tetrahydrofuran (THF) or 1,4-dioxane; alcohols, for example isopropanol or ethylene glycol; amides, for example N,N-dimethylformamide (DMF) or N-methylpyrrolidinone; and nitriles, for example acetonitrile or butyronitrile.

Neither of the above two processes A or B has a critical operating pressure, but they are operable over a wide pressure range, subject only to considerations of economy and materials of construction. It is most convenient, however, to conduct the reaction at approximately atmospheric pressure.

The 5-substituted-3-phenyl-imidazolidine-2,4-diones produced by either of the above two processes A and B can be recovered from the reaction mixture by any conventional technique. Examples of such techniques are solvent extraction and crystallization.

The following are examples of compounds which have been synthesized by the procedures described above. These examples are offered strictly for purposes of illustration, and are intended neither to limit nor to define the invention in any manner.

EXAMPLE 1

This example illustrates the preparation of 5-benzyl-3-(2,5-difluorophenyl)-1-methylimidazolidine-2,4-dione.

2,5-Difluorophenylisocyanate (1.55 g, 10.0 mmol) in methylene chloride (25 mL) was added dropwise to a suspension of phenylalanine (1.65 g, 10.0 mmo) in methylene chloride (50 mL) containing triethylamine (1.4 mL, 1.01 g, 10.0 mmol). The solution was allowed to stir overnight, and was then concentrated. The residue was taken up into 6N HCl and heated to reflux for 3 hours. The cooled solution was extracted with ethyl acetate (3×), and the combined extracts where washed with water (2×), dried (over MgSO₄), filtered and concentrated to give 2.7 grams. Purification by column chromatography gave 2.5 grams of 5-benzyl-3-(2,5-difluorophenyl)imidazolidine-2,4-dione.

5-Benzyl-3-(2,5-difluorophenyl)imidazolidine-2,4-dione (2.0 g, 6.62 mmol) in DMF (10 mL) was added dropwise to a suspension of sodium hydride (166 mg, 6.95 mmol) in DMF (5 mL) at 0° C. The solution was stirred for 1 hour; then methyl iodide (0.62 mL, 9.9 mmol) was added and the mixture was stirred for 5 hours, then diluted with water and extracted with ethyl acetate (3×). The combined extracts were washed with brine (saturated), dried (over MgSO₄), filtered and concentrated to give 1.19 grams of 5-benzyl-3-(2,5-difluorophenyl)-1-methylimidazolidine-2,4-dione, as an oil (compound 1 under Table A).

The structure of the final product was confirmed by nuclear magnetic resonance (NMR), infrared spectra (IR) and mass spectrometry (MS).

EXAMPLE 2

This example illustrates the preparation of 5-(2'-methylpropyl)-3-(2,5-difluorophenyl)-1-methylimidazolidine-2,4-dione.

2,5-Difluorophenylisocyanate (1.55 g, 10.0 mmol) in methylene chloride (25 mL) was added dropwise to a suspension of L-leucine (4.0 g, 30.5 mmol) in methylene chloride (100 mL) containing triethylamine (5.0 mL, 3.63 g, 36.0 mmol) at room temperature. The solution was allowed to stir overnight, then concentrated and the residue heated under reflux in 6N HCl (100 mL) for 2 hours. The cooled mixture was extracted with ethyl acetate (3×), and the combined extracts were washed with sodium bicarbonate (saturated) and then with brine (saturated), dried (over MgSO₄), filtered and concentrated to give 8.8 grams of material which was purified by column chromatography to give 5-(2'-methylpropyl)-3-(2,5-difluorophenyl)imidazolidine-2,4-dione (4.2 grams).

5-(2'-Methylpropyl)-3-(2,5-difluorophenyl)imidazolidine-2,4-dione (3.0 g, 11.1 mmol) in DMF (15 mL) was added dropwise to an ice-cold suspension of sodium hydride (0.30 g, 12.5 mmol) in DMF (4 mL). The solution was allowed to stir for 2 hours, after which methyl iodide (1.04 mL, 2.38 g, 16.8 mmol) in DMF (5 mL) was added dropwise. The solution was stirred overnight and then diluted with water. The product was extracted with ethyl acetate (3×), and the combined extracts were washed with brine (saturated), dried (over MgSO₄), filtered and concentrated. Purification by column chromatography gave 2.7 grams of 5-(2'-methylpropyl)-3-(2,5-difluorophenyl)-1-methylimidazolidine-2,4-dione, as an oil (compound 3 under Table A).

The structure of the final product was confirmed by NMR, IR and MS.

EXAMPLE 3

This example illustrates the preparation of 5-(2-fluorobenzylidene)-3-(2,5-difluorophenyl)-1-methylimidazolidine-2,4-dione.

Acetyl chloride (1.05 equivalent) in methylene chloride (50 mL) was added dropwise to a solution of 3-(2,5-difluorophenyl)imidazolidine-2,4-dione (50 mmol) in methylene chloride (150 mL) containing triethylamine (1.1 equivalent) and a catalytic amount of dimethylaminopyridine. The solution was allowed to stir overnight at room temperature, then was diluted with methylene chloride, and washed with 10% HCl, with water and with brine (saturated), dried (MgSO4), filtered and concentrated to give N-acetyl-3-(2,5-difluorophenyl)imidazolidine-2,4-dione.

N-acetyl-3-(2,5-difluorophenyl)imidazolidine-2,4-dione (2.29 g, 8.65 mmol), 2-fluorobenzaldehyde (1.13 g, 9.1 mmol) and triethylamine (1.75 g, 17.3 mmol) were heated under reflux in DMF (15 mL) for 3 hours. The solution was cooled, diluted with water and extracted with ethyl acetate (3×). The combined extracts were washed with brine (saturated), dried (over MgSO4), filtered, concentrated, and purified by column chromatography to give 1.4 grams of 5-(2-fluorobenzylidene)-3-(2,5-difluorophenyl)imidazolidine-2,4-dione, m.p. 180°–183° C.

The 5-(2-fluorobenzylidene)-3-(2,5-difluorophenyl)imidazolidine-2,4-dione (1.25 g, 3.9 mmol), cesium carbonate (0.67 g, 2.06 mmol) and methyl iodide (0.84 g, 5.9 mmol) were allowed to stir overnight in DMF (15 mL), under a N2 atmosphere. The resulting solution was diluted with water and extracted with ethyl acetate (3×). The combined extracts were washed with brine (saturated), dried (over MgSO4), filtered and concentrated to give 1.3 grams of 5-(2-fluorobenzylidene)-3-(2,5-difluorophenyl)-1-methylimidazolidine-2,4-dione m.p. 94°–97° C. (compound 106 under Table B).

The structure of the final product was confirmed by NMR, IR and MS.

EXAMPLE 4

This example illustrates the preparation of 5-(4-methylbenzylidene)-3-(2,5-difluorophenyl)-1-methylimidazolidine-2,4-dione.

N-acetyl-3-(2,5-difluorophenyl)imidazolidine-2,4-dione (2.1 g, 8.2 mmol), 4-methylbenzaldehyde (1.05 g, 8.7 mmol) and triethylamine (1.7 g, 16.5 mmol) were heated under reflux in DMF (20 mL) for 4 hours. The solution was cooled diluted with water and extracted with ethyl acetate (3×). The combined extracts were washed with brine (saturated), dried (over MgSO4), filtered and concentrated to give 2.3 grams of 5-(4-methylbenzylidene)-3-(2,5-difluorophenyl)imidazolidine-2,4-dione, m.p. 218°–224° C.

The 5-(4-methylbenzylidene)-3-(2,5-difluorophenyl)imidazolidine-2,4-dione (2.25 g, 7.16 mmol), cesium carbonate (1.22 g, 3.76 mmol) and methyl iodide (1.5 g, 3.76 mmol) were stirred together in DMF (20 mL) overnight. The solution was then diluted with water and extracted with ethyl acetate (3×). The combined extracts were washed with brine (saturated), dried (over MgSO4), filtered and concentrated to give 2.3 grams of 5-(4-methylbenzylidene)-3-(2,5-difluorophenyl)-1-methylimidazolidine-2,4-dione, m.p. 136°–140° C. (compound 104 under Table B).

The structure of the above final product was confirmed by NMR, IR and MS.

EXAMPLE 5

This example illustrates the preparation of 5-cyclohexylmethylene-3-(2-fluorophenyl)-1-methylimidazolidine-2,4-dione.

Potassium tert-butoxide (1.12 g, 10.0 mmol) was added in one portion to a solution of N-acetyl-3-(2-fluorophenyl)imidazolidine-2,4-dione (2.36 g, 10.0 mmol) and cyclohexanecarboxaldehyde (1.23 g, 11.0 mmol) in DMF (10 mL) at 0° C. The solution was allowed to warm to RT overnight with stirring, then diluted with water and extracted with ethyl acetate. The combined extracts were washed with brine (saturated), dried (over MgSO4), filtered and concentrated. The crude product was recrystallized from hexane/ethyl acetate to give 5-cyclohexylmethylene-3-(2-fluorophenyl)imidazolidine-2,4-dione, as a white solid.

The 5-cyclohexylmethylene-3-(2-fluorophenyl)imidazolidine-2,4-dione (2.25 g, 7.81 mmol), cesium carbonate (2.6 g, 8.0 mmol) and methyl iodide (1.66 g, 11.7 mmol) were stirred overnight in DMF (25 mL). The solution was diluted with water and extracted with ethyl acetate (3×). The combined extracts were washed with brine (saturated, 2×), dried (over MgSO4), filtered and concentrated. Purification by column chromatography afforded 1.9 grams of 5-cyclohexylmethylene-3-(2-fluorophenyl)-1-methylimidazolidine-2,4-dione, a white solid, m.p. 131°–137° C.

The structure of the above product was confirmed by NMR, IR and MS.

These and further compounds prepared by similar procedures are listed in Tables A and B below, together with physical data in the form of refractive indices or melting points where such measurements were possible, and physical descriptions where they were not.

TABLE A
COMPOUNDS

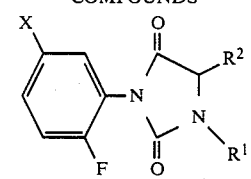

| No. | X | R1 | R2 | $n_D^{30}$ or m.p. °C. |
|---|---|---|---|---|
| 1 | F | CH3 | benzyl | oil |
| 2 | F | CH3 | sec-butyl | oil |
| 3 | F | CH3 | isobutyl | oil |
| 4 | F | CH3 | isopropyl | oil |

TABLE B

COMPOUNDS $$\begin{array}{c}\text{structure with X on phenyl ring, F on phenyl ring, N-CH}_2\text{-N(R}^1\text{) ring with two C=O groups and =CH-R}^3\end{array}$$

| No. | X | R¹ | R³ | $n_D^{30}$ or m.p. °C. |
|---|---|---|---|---|
| 101 | F | CH₃ | phenyl | 108–110 |
| 102 | F | CH₂CH₃ | phenyl | oil |
| 103 | F | CH₃ | 4-Cl-phenyl | 138–140 |
| 104 | F | CH₃ | 4-CH₃-phenyl | 136–140 |
| 105 | F | CH₃ | 4-OCH₃-phenyl | 110–112 |
| 106 | F | CH₃ | 2-F-phenyl | 94–97 |
| 107 | F | CH₃ | 3-pyridyl | 151–156 |
| 108 | F | CH₃ | 3-CF₃-phenyl | 148–150 |
| 109 | F | CH₃ | cyclohexyl | 85–108 |
| 110 | F | CH₃ | 3,4-methylenedioxy-phenyl | 165–167 |
| 111 | H | CH₃ | cyclohexyl | 131–137 |
| 112 | H | CH₃ | styryl | |

The compounds listed in the foregoing tables were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

The test procedures used are as follows:

Pre-Emergence Herbicidal Evaluation at 4 lb/acre

Planting flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were yellow foxtail (*Setaria viridis*), watergrass (*Echinochloa crusgalli*) and wild oat (*Avena fatua*). Broadleaf weeds utilized were annual morningglory (*Ipomoea purpurea*), velvetleaf (*Abutilon theophrasti*), wild mustard (*Brassica kaber*), and curly dock (*Rumex crispus*).

Solutions of the test compounds were made by weighing out 333 mg of the test compound into a 60-mL wide-mouth bottle, then dissolving the compound in 25 mL of acetone containing 1% Tween® 20 (polyoxyethylene sorbitan monolaurate emulsifier). Additional solvents, not exceeding 5 mL, were used if needed to dissolve the compound. A 20.5-mL aliquot was then taken from the solution and diluted with 25 mL of an acetone:water mixture (19:1) containing 1% Tween® 20. This was used as the spray solution.

One day after planting, the flats were sprayed with the spray solution at a rate of 80 gallons of solution per acre with the compound being applied at a rate of 4 pounds per acre (4.48 kg/hectare).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; a dash indicates that no test was performed at that level of application.

Post-Emergence Herbicidal Evaluation at 4 lb/acre

The soil was prepared and seeded with the same varieties used in the pre-emergence test. The flats were placed in the greenhouse at 70–85° F. (21°–29° C.) and watered by sprinkling. Twelve to fourteen days after planting, the flats were sprayed at a rate of 80 gallons of solution per acre. Each compound was applied at the rate of 4 pounds/acre (4.48 kg/hectare), using a spray solution prepared as in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds, with yellow nutsedge listed separately, in both pre-and post-emergence evaluations.

TABLE C

HERBICIDE TEST RESULTS
PERCENT CONTROL AT 4 LB/ACRE

Abbreviations: YNS: Yellow Nutsedge
AVG: Grasses averaged
AVB: Broadleaf weeds averaged

| Compound | Pre-Emergence | | | Post-Emergence | | |
|---|---|---|---|---|---|---|
| No. | YNS | AVG | AVB | YNS | AVG | AVB |
| 1 | 0 | 98 | 100 | 100 | 100 | 100 |
| 2 | 0 | 50 | 100 | 0 | 0 | 70 |
| 3 | 0 | 100 | 100 | 0 | 67 | 100 |
| 4 | 0 | 0 | 93 | 0 | 0 | 87 |
| 101 | 0 | 53 | 37 | 0 | 53 | 100 |
| 102 | 0 | 50 | 100 | 0 | 0 | 70 |
| 103 | 0 | 0 | 63 | 0 | 0 | 33 |
| 104 | 0 | 10 | 100 | 0 | 0 | 100 |
| 105 | 0 | 10 | 93 | 0 | 0 | 100 |
| 106 | 0 | 10 | 100 | 0 | 0 | 100 |
| 107 | 0 | 97 | 100 | 0 | 0 | 100 |
| 108 | 0 | 33 | 97 | 0 | 0 | 57 |
| 109 | 10 | 100 | 100 | 0 | 100 | 100 |
| 110 | 0 | 10 | 20 | 0 | 0 | 0 |
| 111 | 0 | 0 | 20 | 0 | 0 | 65 |
| 112 | 0 | 0 | 55 | 0 | 10 | 67 |

Herbicidal and Crop Injury Tests at 0.25–2.0 lb/acre

Pre-emergence and post-emergence tests were performed at appliation rates ranging from 0.10 to 2.00 lb/acre based on the active ingedient (0.112 to 2.24 kg/hectare) for a number of the compounds listed in Tables A or B. This round of testing extended to both weed and crop species, and followed the same general procedure as the 4 lb/acre tests, exept for the plant species used. The species were as follows:

| | | |
|---|---|---|
| Grass weeds: | yellow foxtail | *Setaria viridis* |
| | annual ryegrass | *Lolium multiflorum* |
| | watergrass | *Echinochloa crusgalli* |
| | shattercane | *Sorghum bicolor* |
| | wild oat | *Avena fatua* |
| | broadleaf | *Brachiaria platyphylla* |
| Broadleaf | annual morningglory | *Ipomoea purpurea* |
| weeds: | cocklebur | *Xanthium pensylvanicum* |
| | sesbania | *Sesbania exasperata* |
| | velvetleaf | *Abutilon theophrasti* |
| | sicklepod | *Cassia obtusifolia* |
| Other: | yellow nutsedge | *Cyperus esculentus* |
| Crops: | cotton | *Gossypium herbaceum* |
| | soybean | *Glycine max* |
| | corn | *Zea mays* |
| | milo | *Sorghum vulgare* |
| | wheat | *Triticum aestivum* |
| | rice | *Oryza sativa* |
| | sugarbeet | *Beta vulgaris* |

The results of these tests are listed in Table D, in which the indicia used are the same as those in Table C.

TABLE D
HERBICIDE AND CROP INJURY TEST RESULTS
PERCENT CONTROL AT 2 LB/ACRE AND LESS

| | Crops* | | | | | | | Weeds | | |
|---|---|---|---|---|---|---|---|---|---|---|
| Rate | (1) | (2) | (3) | (4) | (5) | (6) | (7) | YNS | AVG | AVB |
| Compound No. 1 Pre-Emergence: | | | | | | | | | | |
| 2.00 | 100 | 35 | 30 | 100 | 100 | 35 | 100 | 10 | 68 | 98 |
| 1.00 | 100 | 30 | 20 | 80 | 100 | 0 | 10 | 10 | 33 | 95 |
| 0.50 | 50 | 5 | 0 | 0 | 80 | 0 | 0 | 0 | 0 | 82 |
| Compound No. 1 - Post-Emergence: | | | | | | | | | | |
| 2.00 | 5 | 5 | 10 | 5 | 100 | 0 | 0 | 0 | 2 | 65 |
| 1.00 | 5 | 5 | 10 | 0 | 90 | 0 | 0 | 0 | 0 | 46 |
| 0.50 | 0 | 0 | 5 | 0 | 30 | 0 | 0 | 0 | 0 | 18 |
| Compound No. 3 - Pre-Emergence: | | | | | | | | | | |
| 2.00 | 100 | 100 | 100 | 100 | 100 | 75 | 40 | 35 | 95 | 99 |
| Compound No. 3 - Post-Emergence: | | | | | | | | | | |
| 2.00 | 5 | 10 | 15 | 0 | 100 | 0 | 0 | 15 | 5 | 88 |
| Compound No. 101 - Pre-Emergence: | | | | | | | | | | |
| 2.00 | 35 | 0 | 0 | 20 | 100 | 0 | 0 | 10 | 51 | 70 |
| Compound No. 101 - Post-Emergence: | | | | | | | | | | |
| 2.00 | 75 | 0 | 0 | 0 | 100 | 0 | 15 | 0 | 0 | 77 |
| 1.00 | 70 | 0 | 0 | 0 | 90 | 0 | — | 0 | — | 75 |
| 0.50 | 40 | 0 | 0 | 0 | 85 | 0 | 0 | 0 | 0 | 8 |
| Compound No. 105 - Pre-Emergence: | | | | | | | | | | |
| 2.00 | 100 | 35 | 65 | 95 | 100 | 20 | 15 | 10 | 75 | 96 |
| 1.00 | 90 | 0 | 15 | 80 | 100 | 0 | 0 | 0 | 47 | 94 |
| 0.50 | 5 | 0 | 0 | 25 | 75 | 0 | 0 | 0 | 0 | 72 |
| Compound No. 105 - Post-Emergence: | | | | | | | | | | |
| 2.00 | 75 | 5 | 5 | 15 | 100 | 0 | 25 | 0 | 5 | 86 |
| 1.00 | 15 | 5 | 5 | 15 | 100 | 0 | 5 | 0 | 2 | 69 |
| 0.50 | 15 | 5 | 5 | 15 | 100 | 0 | 0 | 0 | 1 | 33 |
| Compound No. 107 - Pre-Emergence: | | | | | | | | | | |
| 2.00 | 100 | 10 | 10 | 25 | 100 | 0 | 15 | 0 | 43 | 97 |
| 1.00 | 35 | 0 | 0 | 0 | 95 | 0 | 0 | 0 | 13 | 74 |
| 0.50 | 5 | 0 | 0 | 0 | 50 | 0 | 0 | 0 | 5 | 3 |
| Compound No. 107 - Post-Emergence: | | | | | | | | | | |
| 2.00 | 90 | 15 | 15 | 30 | 100 | 0 | 30 | 5 | 6 | 98 |
| 1.00 | 70 | 10 | 15 | 15 | 100 | 0 | 30 | 0 | 3 | 69 |
| 0.50 | 15 | 5 | 5 | 15 | 100 | 0 | 15 | 0 | 0 | 44 |

* Crops:
(1) Soybean
(2) Wheat
(3) Milo
(4) Rice
(5) Sugarbeet
(6) Corn
(7) Cotton The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows secape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed be extrusion, agglomeration or prilling, or are naturally occurring. Examples of such materials are vermiculite, sintered clay, kaolin, attapulgite clay, sawdust and granular carbon. Shell or membrane materials, styrene-butadiene copolymers, polyacrylontiriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprise from about 5% to about 95% of the active ingredients in the formulations. These combinations frequently provide a higher level of effectiveness in controlling weeds and often provide results unattainable with seperate formulations of the individual herbicides.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral urea, chloroxuron, cycluron, fenuron, monuron, monuron TCA, diuron, linuron, monolinuron neburon, buturon and timetruron;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6-trichlorophenylacetic acid and 2,4-dichloro-3-nitrobenzoic acid;

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocial, postassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following the are examples of typical formulations.

5% dust:

5 parts active compound
95 parts talc
2% dust:
2 parts active compound
1 part highly dispersed silicic acid
97 parts talc These dusts are formed by mixing the components then grinding the mixture to the desired particle size.

5% granules:
5 parts active compound
0.25 part epichlorohydrin
0.25 part cetyl polyglycol ether
3.5 parts polyethylene glycol
91 parts kaolin (particle size 0.3–0.8 mm)

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo. wettable powders:

70%:
70 parts active compound
5 parts sodium dibutylnaphthylsulfonate
3 parts naphthalenesulfonic acid/phenolsulfonic acid/formaldehyde condensate (3:2:1)
10 parts kaolin
12 parts Champagne chalk 40%:
40 parts active compound
5 parts sodium lignin sulfonate
1 part sodium dibutylnaphthalenesulfonic acid
54 parts silicic acid 25%:
25 parts active compound
4.5 parts calcium lignin sulfate
1.9 parts Champagne chalk/hydroxyethyl cellulose (1:1)
1.5 parts sodium dibutylnaphthalenesulfonate
19.5 parts silicic acid
19.5 parts Champagne chalk
28.1 parts kaolin 25%:
25 parts active compound
2.5 parts isooctylphenoxy-polyethylene-ethanol
1.7 parts Champagne chalk/hydroxyethyl cellulose (1:1)
8.3 parts sodium aluminum silicate
16.5 parts kieselguhr
46 parts kaolin 10%:
10 parts active compound
3 parts of a mixture of sodium salts of saturated fatty alcohol sulfates
5 parts naphthalenesulfonic acid/formaldehyde condensate
82 parts kaolin These wettable powders are prepared by intimately mixing the active compounds with the additives in suitable mixers, and grinding the resulting mixtures in mills or rollers.

25% emulsifiable concentrate:
25 parts active substance
2.5 parts epoxidized vegetable oil
10 parts of an alkylarlsulfonate/fatty alcohol polyglycol ether mixture
5 parts dimethylformamide
57.5 parts xylene

What is claimed is:

1. An herbicidal composition comprising:
   (a) an herbicidally effective amount of a compound having the formula

[chemical structure]

in which:
   X is halogen;
   R is =CH—$R^3$;
   $R^1$ is methyl or ethyl; and
   $R^3$ is $C_{1-8}$ alkyl, $C_{3-8}$ cycloalkyl, phenyl, substituted phenyl, benzyl, substituted benzyl, or an aromatic heterocyclic group of 3 to 10 ring atoms; and
   (b) an herbicidally suitable inert diluent or carrier.

2. An herbicidal composition according to claim 1 wherein X is fluoro.

3. An herbicidal composition according to claim 2 wherein said compound has the formula

[chemical structure]

4. An herbicidal composition according to claim 3 wherein $R^3$ is cyclohexyl, pyridyl, phenyl or substituted phenyl.

5. An herbicidal composition according to claim 4 wherein said substituted phenyl is substituted at the 2, 3 or 4 position with chloro, fluoro, methyl, methoxy or trifluoromethyl.

6. An herbicidal composition comprising:
   (a) an herbicidally effective amount of a compound having the formula

[chemical structure]

in which:
   $R^2$ is methyl or ethyl; and
   $R^3$ is cyclohexyl or styryl; and
   (b) an herbicidally suitable inert diluent or carrier.

7. A method of controlling undesirable vegetation comprising applying to said vegetation or to the locus thereof an herbicidally effective amount of a compound having the formula

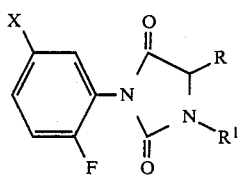

in which:

X is halogen;

R is =CH—R³

R¹ is methyl or ethyl; and

R³ is $C_{1-8}$ alkly, $C_{3-8}$ cycloalkyl, phenyl, substituted phenyl, benzyl, substituted benzyl, or an aromatic heterocyclic group of 3 to 10 ring atoms.

8. A method according to claim 7 wherein X is fluoro.

9. A method according to claim 8 wherein said compound has the formula

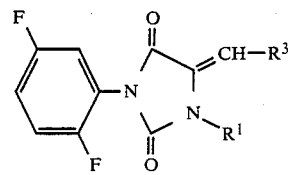

10. A method according to claim 9 wherein R³ is cyclohexyl, pyridyl, phenyl or substituted phenyl.

11. A method according to claim 10 wherein said substituted phenyl is substituted at the 2, 3 or 4 position with chloro, fluoro, methyl, methoxy or trifluoromethyl.

12. A method of controlling undesirable vegetation comprising applying to said vegetation or to the locus thereof an herbicidally effective amount of a compound having the formula

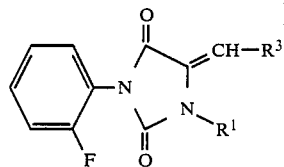

in which:
R¹ is methyl or ethyl; and
R³ is cyclohexyl or styryl.

* * * * *